United States Patent [19]

Kenton

[11] Patent Number: 4,484,017
[45] Date of Patent: Nov. 20, 1984

[54] OLEFIN AROMATIZATION PROCESS

[75] Inventor: Joseph R. Kenton, Bartlesville, Okla.

[73] Assignee: Phillips Petroleum Company, Bartlesville, Okla.

[21] Appl. No.: 589,258

[22] Filed: Mar. 13, 1984

Related U.S. Application Data

[62] Division of Ser. No. 518,862, Aug. 1, 1983.

[51] Int. Cl.³ .............. C07C 2/00; C10G 35/04; B01J 23/10
[52] U.S. Cl. .................. 585/415; 585/417; 585/418; 208/134; 502/302; 502/304
[58] Field of Search .............. 585/415, 417, 418; 208/134; 502/302, 304

[56] References Cited

U.S. PATENT DOCUMENTS

| 1,207,707 | 12/1916 | Bosch | 502/302 |
| 2,990,434 | 6/1961 | Smith | 585/417 |
| 3,168,584 | 2/1965 | Nager | 260/673 |
| 3,275,706 | 9/1966 | Stapp | 260/683.15 |
| 3,374,282 | 3/1968 | Soderquist et al. | 260/673.5 |
| 3,456,030 | 7/1969 | Crane et al. | 260/680 |
| 3,494,956 | 2/1970 | Greene et al. | 260/465.8 |
| 3,548,021 | 12/1970 | Brattesani | 260/673.5 |
| 3,631,216 | 12/1971 | Lipsig | 260/680 R |
| 3,644,551 | 2/1972 | Ondrey et al. | 260/673 |
| 3,730,957 | 5/1973 | Bozik et al. | 585/417 |
| 3,761,536 | 9/1973 | Bozik et al. | 260/680 R |
| 3,769,361 | 10/1978 | Friedli | 260/673 |
| 3,830,866 | 8/1974 | D'Alessandro et al. | 260/673 |
| 3,963,793 | 6/1976 | Weterings | 260/668 R |
| 3,981,795 | 9/1976 | Antos | 585/417 |
| 4,001,317 | 1/1977 | Grasselli et al. | 502/304 |
| 4,146,734 | 3/1979 | Slinkard | 502/304 |
| 4,148,757 | 4/1979 | Brazdil et al. | 502/304 |
| 4,151,071 | 4/1979 | Myers | 208/135 |
| 4,169,865 | 10/1979 | Bamforth et al. | 585/314 |
| 4,254,293 | 3/1981 | Tremont et al. | 502/304 |

FOREIGN PATENT DOCUMENTS

| 453615 | 12/1948 | Canada | 585/415 |
| 55-15445 | 4/1980 | Japan . | |
| 2000178A | 1/1979 | United Kingdom . | |
| 2000179A | 1/1979 | United Kingdom . | |

OTHER PUBLICATIONS

F. Solymosi and F. Bozo, "The Oxidative Dehydrodimerization and Aromatization of Propylene on $SnO_2$-$Bi_2O_3$ Binary Oxides", Proc. of Int. Cong. Catalysis, 6th, (1976), 1, pp. 365–375.

Mireya R. Goldwasser and David L. Trimm, "The Oxidation of Isobutene to p-Xylene over Bismuth Oxide-based Catalysts", J. Appl. Chem. Biotechol., 1978, 28, pp. 733–739.

H. E. Swift, J. E. Bozik and J. A. Ondrey, "Dehydrodimerization of Propylene Using Bismuth Oxide as the Oxidant", Journal of Catalysis, 21, (1971), pp. 212–224.

Swift and Bozik, note entitled "Automatization of Lower Olefins", Journal of Catalysis, 22, (1971), pp. 427–429.

Primary Examiner—Delbert E. Gantz
Assistant Examiner—Chung K. Pak
Attorney, Agent, or Firm—L. M. Lavin

[57] ABSTRACT

The conversion of unsaturated compounds to aromatic compounds is carried out using a catalyst comprising bismuth and lanthanide components.

7 Claims, No Drawings

OLEFIN AROMATIZATION PROCESS

This application is a divisional application of my copending application, Ser. No. 518,862 filed Aug. 1, 1983.

BACKGROUND OF THE INVENTION

The dehydrocyclization of unsaturated aliphatic compounds to produce aromatic compounds is well-known. The aromatic species produced are useful as solvents, plasticizers, and as anti-knock components in fuels.

Bismuth oxides are widely used as catalysts for dehydrocyclization. However, its use suffers from severe drawbacks. Among them are low conversion and selectivity values.

THE INVENTION

The invention deals with the production of cyclic organic compounds via catalytic dehydrocyclization. It has been discovered that the addition of beneficiating amounts of a lanthanide element-containing substance to a conventional bismuth dehydrocyclization catalyst, with optional base treatment of the mixture, improves reaction efficiency.

In one embodiment, propylene is converted to benzene in the presence of a catalyst containing bismuth and cerium oxides. Minimal amounts of hexadiene, i.e. propylene dehydrocoupling product, are formed. Conversions of 50 to 70% and selectivities of up to 85 to 90% are observed.

OBJECTS OF THE INVENTION

It is an object of the invention to provide a catalyst useful for the conversion of olefins to aromatics.

It is another object to provide a process for the conversion of olefins to aromatics using the catalyst of the invention.

ADVANTAGES

The catalysts and process of the invention have several advantages over the prior art. The selectivity of the reaction, i.e. the proportion of desired aromatic species in the product, is greater than 75%, with selectivities of up to 85 to 90% being achieved. The degree of conversion, or the extent to which the olefin reactant(s) is (are) consumed, will generally be greater than 50%, with conversions of 50–70% being typical.

In addition, the production of undesired by-products, such as non-cyclic intermediates, carbon monoxide, and carbon dioxide, is minimized when the catalyst of the invention is used.

Other advantages and objects of the invention will become apparent upon consideration of the description and claims.

DESCRIPTION OF THE INVENTION

Olefin Feedstock

The catalysts of the invention are useful for dehydrocyclizing or reforming propylene.

The Catalyst Composition

The inventive catalysts contain a grouping of metal ingredients which, when combined, yield catalytic effects during the production of cyclic compounds from non-cyclic ones. Typical catalysts contain at least one bismuth component and at least one lanthanide component.

(A) The Bismuth Component

The bismuth components useful herein are those which exhibit catalytic effects in the dehydrocyclization of olefins. Generally, they are compounds of trivalent bismuth. Useful substances include alkali metal bismuthates, oxides of bismuth, and compounds convertible thereto. Bismuth oxide, e.g. $Bi_2O_3$, is preferred. Mixtures of bismuth-containing substances are operable.

The quantity of bismuth component in the total catalyst can vary greatly. Generally, the molar ratio of bismuth component to lanthanide component will be from about 5:1 to about 1:5, with about 2:1 to about 1:2 preferred.

(B) The Lanthanide Component

The lanthanide component used contains one or more substances or elements categorized as "rare earth", which substance exerts a beneficiating affect on the dehydrocyclization process. Generally, the materials used in component (B) will contain one or more of lanthanum, cerium, neodymium, terbium, yttrium, and the like. Cerium is preferred.

Useful anionic portions of the lanthanide component include nitrates, sulfates, hydroxides, oxides and the like. Oxides are generally preferred. Cerium oxide, $CeO_2$, is highly preferred.

Mixtures of lanthanide-containing substances can be used.

When a base-treated catalyst is to be employed, the metal hydroxide or other alkaline reagent is generally employed in sufficient quantity to provide approximately equimolar quantities of each metal component (including base) in the catalyst.

Catalyst Preparation

A typical catalyst preparation is described in Example IV below.

Generally, the catalyst can be prepared using any suitable method including dry mixing and co-precipitation.

In one embodiment the catalyst is treated with a base, such as an inorganic alkaline substance. Typical alkaline reagents include the oxides, hydroxides, and carbonates of alkali and alkaline earth metals. Alkali metal oxides and hydroxides are preferred.

Suitable methods for base treatment include dry mixing, co-precipitation and other conventional methods.

Dehydrocyclization Conditions

The conditions under which unsaturated molecules are converted to cyclic ones are generally well-known in the art, however, for purposes of illustration applicant sets forth parameters from which the skilled artisan can extrapolate.

Reaction pressures are those conventionally used for dehydrocyclization. While atmospheric pressure, or other pressures on that order, is generally employed, higher pressures are operable.

Generally, temperatures of about 300° to about 600° C. are operable, with temperatures of about 450° to about 600° C. preferred, and about 450° to about 550° highly preferred. Incremental elevation of reaction temperature is often employed.

The contacting of reactant gas with catalyst generally takes place at a gas hourly space velocity (GHSV) or vapor hourly space velocity (VHSV) of about 50 to about 500 with a GHSV of about 200 preferred.

A typical operation is demonstrated by the following procedure.

GENERAL PROCEDURE

An electrically heated 20"×½" tubular reactor (316SS) containing a thermocouple well was used for all of the experiments. Temperatures were controlled by a Thermo Electric 400 proportioning temperature controller. The catalyst (23 mL) occupied the middle portion of the reactor with glass beads placed in the top and bottom sections. Flowmeters were used to measure the flow of propylene, nitrogen, and air (or oxygen).

In a typical experiment, 23 mL of catalyst were charged to the reactor. The reactor was heated to 350° C. and propylene gas (atmospheric pressure) was fed to the reactor at a rate of 81 mL/minute (210 VHSV). The reactor effluent gas was sampled for gas liquid chromatograph (glc) analysis in a heated syringe after being on stream 1 minute. The heated syringe was evacuated to remove volatile contaminants and another gas sample was taken after the reactor was on stream for 6 minutes. Propylene flow was discontinued and the reactor was purged for 10 minutes with nitrogen at 320 mL/min. to remove volatile compounds. The catalyst was then oxidized with air flowing at 160 mL/min for 30 minutes. Air flow was discontinued and the reactor was purged with nitrogen at 320 mL/min. for 10 minutes before starting another reaction cycle. The catalysts were usually evaluated at 350°, 400°, 450°, 500° and 550° C. Longer reaction cycles were made when appropriate.

Product analyses were made using a Hewlett-Packard Model 7620A Research Chromatograph or a Hewlett-Packard 5880A chromatograph. Both units were equipped with a 20'×⅛" column packed with OV101 column packing.

EXAMPLES

Example I

Catalyst Preparation

All catalysts employed were prepared by one of two methods. Commercially available metal oxides were mixed in powder form, in some cases further treated with an aqueous solution of an alkali metal compound, and evaporated to dryness. A pellet die lubricant such as graphite was added to the dried, mixed powders and ⅛" pellets were prepared using a Stokes Model 1A pellet mill. Pellets were typically calcined in an air atmosphere at 550° C. prior to use.

Alternatively, catalysts were prepared by a precipitation technique. Thus, suitable metal compounds such as Bi(NO$_3$)$_3$.5H$_2$O or Ce(NO$_3$)$_3$.6H$_2$O were dissolved in water containing enough of a suitable acid such as HNO$_3$ to ensure dissolution of the metal compounds. The acidic metal-containing solution and an ammonium hydroxide solution were then added slowly and concurrently to a stirred vessel at such a rate as to maintain a pH of the final mixture of about 9. Once all the metal-containing solution had been added, the mixed metal hydroxide precipitate was collected by vacuum filtration and washed with deionized water. If an alkali metal compound was desired as an additional catalyst component, the wet, washed filter cake was then slurried with a solution of the alkali metal compound, thoroughly mixed, then oven dried. The dried catalyst was crushed into a powder, passed through a 40 mesh sieve, treated with a die lubricant and pelletized as above. Pellets were typically calcined in an air atmosphere at 550° C. prior to use.

A number of catalysts were prepared by each technique. Source compounds employed, calcination conditions and final catalyst designation are provided in Table I.

TABLE I

| Catalyst | Composition (metal atomic ratio) | Calcination Time, hr. | Calcination Temp., °C. | Source Compound, mol Ce | Source Compound, mol Bi | Source Compound, mol Misc |
|---|---|---|---|---|---|---|
| (a) Preparation from commercially available metal oxides | | | | | | |
| A | CeO$_2$ | 18 | 500 | CeO$_2$, 0.58 | | |
| B | CeO$_2$/K$_2$CO$_3$ (1:1) | 18 | 550 | CeO$_2$, 0.58 | | K$_2$CO$_3$, 0.29 |
| C | NaBiO$_3$ | 3 | 550 | | NaBiO$_3$, 0.39 | |
| D | NaBiO$_3$/CeO$_2$ (1:1) | 5 | 500 | CeO$_2$, 0.22 | NaBiO$_3$, 0.22 | |
| E | Bi$_2$O$_3$ | 3 | 550 | | Bi$_2$O$_3$ | |
| F | Bi$_2$O$_3$/CeO$_2$ (1:1) | 5 | 500 | CeO$_2$, 0.31 | Bi$_2$O$_3$, 0.15 | |
| G | Bi$_2$O$_3$/CeO$_2$/K$_2$CO$_3$ (1:1:1) | 18 | 550 | CeO$_2$, 0.23 | Bi$_2$O$_3$, 0.12 | K$_2$CO$_3$, 0.12 |
| (b) Preparation by precipitation technique | | | | | | |
| H | Bi$_2$O$_3$ | 3 | 550 | | Bi(NO$_3$)$_3$.5H$_2$O, 0.34 | |
| I | Bi$_2$O$_3$/NaOH (1:1) | 3 | 550 | | Bi(NO$_3$)$_3$.5H$_2$O, 0.34 | NaOH, 0.34 |
| J | Bi$_2$O$_3$/CeO$_2$ (1:1) | 18 | 500 | Ce(NO$_3$)$_3$.6H$_2$O, 0.39 | Bi(NO$_3$)$_3$.5H$_2$O, 0.39 | |
| K | Bi$_2$O$_3$/CeO$_2$/NaOH (1:1:1) | 5 | 500 | Ce(NO$_3$)$_3$.6H$_2$O, 0.18 | Bi(NO$_3$)$_3$.5H$_2$O, 0.18 | NaOH, 0.18 |

Example II

Each of the catalysts A-K prepared and activated as described above were tested for oxidative cyclodehydrogenation activity with propylene feed. Propylene conversion and selectivities to the various analyzed products are summarized for each catalyst in Tables II-XII.

Evaluation of each of the catalysts described reveals that invention catalysts D, G, and K (NaBiO$_3$/CeO$_2$, Bi$_2$O$_3$/CeO$_2$/K$_2$CO$_3$, Bi$_2$O$_3$/CeO$_2$/NaOH, respectively) give benzene in high selectivity (>80%) at propylene conversion of 50% and greater. Other catalysts tested are capable of either high benzene selectivity or high propylene conversion under appropriate reaction conditions, but not both at the same time.

TABLE II

Reaction of Propylene over Catalyst A

| Temp °C. | Sampling Time, min | Propylene Conversion % | % Selectivity to... | | | |
|---|---|---|---|---|---|---|
| | | | $CO + CO_2$ | 1,5-hexadiene | Other hexadienes | Benzene |
| 550 | 1 | 5.1 | 85.8 | 0 | 0 | 14.2 |
| 550 | 4 | 6.3 | 87.6 | 0 | 0 | 12.4 |
| 550 | 11 | 4.1 | 86.6 | 0 | 0 | 13.4 |
| 600 | 4 | 18.9 | 87.9 | 0 | 0 | 12.1 |

TABLE III

Reaction of Propylene over Catalyst B

| Temp °C. | Sampling Time, min | Propylene Conversion % | % Selectivity to... | | | |
|---|---|---|---|---|---|---|
| | | | $CO + CO_2$ | 1,5-hexadiene | Other hexadienes | Benzene |
| 500 | 1 | 1.8 | 3.3 | 5.1 | 21.3 | 70.4 |
| 500 | 3 | 0.6 | 3.5 | 4.6 | 21.9 | 70.0 |
| 550 | 1 | 2.6 | 7.4 | 2.8 | 12.5 | 77.4 |
| 550 | 1 | 2.6 | 7.4 | 2.8 | 12.5 | 77.4 |
| 550 | 3 | 1.7 | 22.3 | 0.8 | 8.5 | 68.3 |
| 600 | 1 | 3.0 | 17.1 | 1.6 | 7.9 | 73.4 |

TABLE IV

Reaction of Propylene over Catalyst C

| Temp °C. | Sampling Time, min | Propylene Conversion % | % Selectivity to... | | | |
|---|---|---|---|---|---|---|
| | | | $CO + CO_2$ | 1,5-hexadiene | Other hexadienes | Benzene |
| 350 | 1 | 0.01 | 0 | ~100 | 0 | 0 |
| 350 | 6 | 0.03 | 0 | 40 | 0 | 60 |
| 400 | 1 | 0.06 | 0 | ~100 | 0 | 0 |
| 400 | 6 | 0.09 | 0 | 51 | 0 | 49 |
| 400 | 15 | 0.07 | 0 | 56 | 0 | 44 |
| 450 | 1 | 2.3 | 1 | 88.2 | 6.6 | 4.3 |
| 450 | 6 | 1.5 | 1.2 | 90.8 | 6.3 | 1.8 |
| 500 | 1 | 4.7 | 1.3 | 87.8 | 3.6 | 7.3 |
| 500 | 6 | 4.4 | 0.8 | 87.2 | 4.5 | 7.4 |
| 550 | 1 | 8.4 | 2.8 | 71.2 | 3.8 | 21.8 |
| 550 | 6 | 4.8 | 2.2 | 80.0 | 7.5 | 10.5 |

TABLE V

Reaction of Propylene over Catalyst D

| Temp °C. | Sampling Time, min | Propylene Conversion % | % Selectivity to... | | | |
|---|---|---|---|---|---|---|
| | | | $CO + CO_2$ | 1,5-hexadiene | Other hexadienes | Benzene |
| 350 | 1 | 0.6 | 0 | 83.4 | 8.3 | 8.3 |
| 350 | 3 | 0.5 | 4.4 | 70.0 | 6.0 | 19.6 |
| 400 | 3 | 1.2 | 8.5 | 76.5 | 5.8 | 9.3 |
| 450 | 1 | 5.2 | 32.3 | 39.1 | 9.6 | 19.0 |
| 450 | 3 | 8.5 | 59.4 | 28.9 | 3.9 | 7.8 |
| 500 | 1 | 32.5 | 42.7 | 3.5 | 3.2 | 50.6 |
| 500 | 3 | 26.8 | 35.7 | 10.6 | 4.6 | 49.1 |
| 500 | 5 | 16.4 | 50.8 | 11.1 | 4.5 | 33.5 |
| 550 | 1 | 45.0 | 5.2 | 1.0 | 1.0 | 92.5 |
| 550 | 3 | 62.6 | 22.6 | 1.4 | 1.3 | 74.7 |
| 550 | 6 | 56.5 | 16.9 | 3.0 | 1.4 | 78.7 |
| 550 | 9 | 50.8 | 13.7 | 2.4 | 1.6 | 82.3 |
| 550 | 12 | 52.7 | 7.37 | 2.0 | 1.5 | 89.2 |
| 550 | 15 | 49.8 | 7.7 | 1.9 | 1.5 | 89.0 |
| 600 | 3 | 60.7 | 33.0 | 1.0 | 1.0 | 65.0 |

TABLE VI

Reaction of Propylene over Catalyst E

| Temp °C. | Sampling Time, min | Propylene Conversion % | % Selectivity to... | | | |
|---|---|---|---|---|---|---|
| | | | $CO + CO_2$ | 1,5-hexadiene | Other hexadienes | Benzene |
| 350 | 1 | 1.0 | 8.6 | 81.2 | 9.4 | 0.8 |
| 350 | 6 | 0.7 | 16.8 | 76.0 | 5.5 | 1.8 |
| 400 | 1 | 3.6 | 15.4 | 73.5 | 8.3 | 2.9 |
| 400 | 6 | 1.8 | 28.7 | 64.5 | 5.4 | 1.4 |
| 450 | 1 | 9.4 | 26.4 | 59.3 | 6.1 | 8.2 |

TABLE VI-continued

Reaction of Propylene over Catalyst E

| Temp °C. | Sampling Time, min | Propylene Conversion % | % Selectivity to... | | | |
|---|---|---|---|---|---|---|
| | | | CO + CO$_2$ | 1,5-hexadiene | Other hexadienes | Benzene |
| 450 | 6 | 8.2 | 29.6 | 58.5 | 5.9 | 6.0 |
| 500 | 1 | 25.4 | 30.4 | 35.5 | 4.5 | 29.7 |
| 500 | 6 | 19.3 | 35.9 | 34.8 | 4.3 | 25.1 |
| 500 | 15 | 24.6 | 24.1 | 38.5 | 5.2 | 32.2 |
| 550 | 1 | 44.5 | 40.2 | 16.0 | 2.5 | 41.3 |
| 550 | 6 | 41.6 | 33.8 | 20.2 | 2.9 | 43.1 |
| 550 | 15 | 31.8 | 43.5 | 20.9 | 2.8 | 32.8 |

TABLE VII

Reaction of Propylene over Catalyst F

| Temp °C. | Sampling Time, min | Propylene Conversion % | % Selectivity to... | | | |
|---|---|---|---|---|---|---|
| | | | CO + CO$_2$ | 1,5-hexadiene | Other hexadienes | Benzene |
| 450 | 1 | 13.4 | 5.3 | 3.1 | 5.7 | 85.8 |
| 450 | 3 | 24.4 | 59.1 | 1.5 | 2.7 | 36.7 |
| 500 | 1 | 62.5 | 44.6 | 2.8 | 1.0 | 54.1 |
| 500 | 3 | 56.2 | 52.2 | 0.5 | 1.2 | 46.1 |
| 500 | 5 | 53.6 | 61.1 | 0.4 | 1.0 | 37.5 |
| 550 | 1 | 88.0 | 53.8 | 0 | 0.1 | 46.0 |
| 550 | 3 | 85.5 | 54.2 | 0.1 | 0.2 | 45.5 |
| 600 | 1 | 98.0 | 69.0 | 0 | 0 | 31.0 |
| 600 | 3 | 95.9 | 76.3 | 0 | 0 | 23.7 |

TABLE VIII

Reaction of Propylene over Catalyst G

| Temp °C. | Sampling Time, min | Propylene Conversion % | % Selectivity to... | | | |
|---|---|---|---|---|---|---|
| | | | CO + CO$_2$ | 1,5-hexadiene | Other hexadienes | Benzene |
| 500 | 1 | 35.6 | 23.8 | 7.1 | 4.4 | 64.7 |
| 500 | 3 | 41.3 | 29.1 | 7.2 | 4.3 | 59.4 |
| 550 | 1 | 69.9 | 13.8 | 1.1 | 1.0 | 84.0 |
| 550 | 3 | 75.8 | 25.1 | 1.4 | 1.3 | 72.3 |
| 600 | 1 | 92.5 | 17.6 | 0.3 | 0.3 | 81.8 |
| 600 | 3 | 84.4 | 26.6 | 0.7 | 0.4 | 72.3 |
| 600 | 6 | 69.3 | 26.4 | 1.0 | 0.5 | 72.1 |
| 600 | 12 | 37.1 | 19.9 | 4.5 | 1.5 | 74.2 |
| 600 | 15 | 10.9 | 40.1 | 24.4 | 7.5 | 27.7 |

TABLE IX

Reaction of Propylene over Catalyst H

| Temp °C. | Sampling Time, min | Propylene Conversion % | % Selectivity to... | | | |
|---|---|---|---|---|---|---|
| | | | CO + CO$_2$ | 1,5-hexadiene | Other hexadienes | Benzene |
| 350 | 1 | 1.2 | 14.8 | 70.5 | 10.0 | 4.8 |
| 350 | 6 | 0.9 | 26.8 | 64.9 | 5.4 | 3.1 |
| 400 | 1 | 5.0 | 25.2 | 56.0 | 10.1 | 8.7 |
| 400 | 6 | 2.9 | 40.2 | 51.6 | 4.9 | 3.3 |
| 450 | 1 | 14.2 | 38.6 | 38.3 | 5.7 | 17.5 |
| 450 | 6 | 12.9 | 41.6 | 39.7 | 6.0 | 12.8 |
| 500 | 1 | 36.9 | 39.7 | 16.3 | 3.9 | 40.1 |
| 500 | 6 | 37.1 | 31.9 | 18.4 | 4.5 | 45.3 |
| 550 | 1 | 55.7 | 43.2 | 9.1 | 1.9 | 45.8 |

TABLE X

Reaction of Propylene over Catalyst I

| Temp °C. | Sampling Time, min | Propylene Conversion % | % Selectivity to... | | | |
|---|---|---|---|---|---|---|
| | | | CO + CO$_2$ | 1,5-hexadiene | Other hexadienes | Benzene |
| 350 | 1 | 0.4 | 1.9 | 93.4 | 4.2 | 0.5 |
| 350 | 6 | 0.5 | 12.0 | 49.0 | 2.7 | 36.3 |
| 400 | 1 | 1.2 | 11.4 | 82.7 | 5.2 | 0.7 |
| 400 | 6 | 0.6 | 19.8 | 69.1 | 7.1 | 4.0 |
| 450 | 1 | 4.5 | 9.8 | 78.1 | 7.9 | 4.1 |
| 450 | 6 | 3.6 | 10.3 | 75.8 | 10.0 | 3.8 |
| 500 | 1 | 12.5 | 12.1 | 66.1 | 5.9 | 16.0 |

TABLE X-continued

Reaction of Propylene over Catalyst I

| Temp °C. | Sampling Time, min | Propylene Conversion % | % Selectivity to... CO + CO₂ | 1,5-hexadiene | Other hexadienes | Benzene |
| --- | --- | --- | --- | --- | --- | --- |
| 500 | 6 | 12.2 | 12.0 | 66.8 | 6.4 | 14.8 |
| 500 | 15 | 11.0 | 12.7 | 68.1 | 6.7 | 12.6 |
| 550 | 1 | 24.3 | 28.5 | 40.1 | 3.9 | 27.3 |
| 550 | 6 | 22.9 | 25.1 | 45.0 | 4.9 | 25.0 |
| 550 | 15 | 17.3 | 23.9 | 52.5 | 6.0 | 17.6 |
| 550 | 6 | 51.5 | 34.5 | 13.3 | 2.4 | 49.7 |
| 550 | 15 | 41.2 | 29.2 | 22.0 | 3.8 | 45.0 |

TABLE XI

Reaction of Propylene over Catalyst J

| Temp °C. | Sampling Time, min | Propylene Conversion % | % Selectivity to... CO + CO₂ | 1,5-hexadiene | Other hexadienes | Benzene |
| --- | --- | --- | --- | --- | --- | --- |
| 350 | 1 | 0.4 | 6.2 | 32.8 | 12.1 | 49.0 |
| 350 | 1 | 0.6 | 6.7 | 29.8 | 23.2 | 40.4 |
| 400 | 1 | 3.3 | 2.2 | 9.0 | 13.1 | 75.6 |
| 400 | 3 | 4.9 | 68.9 | 13.0 | 6.0 | 12.2 |
| 400 | 5 | 7.6 | 83.2 | 8.0 | 2.5 | 6.3 |
| 450 | 1 | 15.3 | 18.4 | 5.1 | 6.2 | 70.3 |
| 450 | 5 | 21.2 | 55.8 | 6.8 | 3.6 | 33.9 |
| 500 | 1 | 59.6 | 60.7 | 0.4 | 0.8 | 38.1 |
| 500 | 3 | 55.6 | 67.2 | 0.5 | 0.9 | 31.4 |
| 550 | 1 | 85.9 | 57.3 | 0.1 | 0.2 | 42.3 |
| 550 | 3 | 73.6 | 56.4 | 0.5 | 0.8 | 42.3 |
| 550 | 5 | 73.1 | 61.9 | 0.2 | 0.3 | 37.6 |
| 600 | 1 | 96.0 | 63.1 | 0.8 | 0.5 | 35.7 |
| 600 | 3 | 90.4 | 69.0 | 0.5 | 0.4 | 30.2 |

TABLE XII

Reaction of Propylene over Catalyst K

| Temp °C. | Sampling Time, min | Propylene Conversion % | % Selectivity to... CO + CO₂ | 1,5-hexadiene | Other hexadienes | Benzene |
| --- | --- | --- | --- | --- | --- | --- |
| 350 | 1 | 1.2 | 0.3 | 80.0 | 4.1 | 15.7 |
| 350 | 3 | 1.6 | 7.8 | 48.1 | 4.2 | 40.1 |
| 400 | 1 | 2.1 | 0 | 89.5 | 7.9 | 3.5 |
| 400 | 3 | 1.8 | 2.5 | 79.3 | 6.1 | 12.1 |
| 450 | 1 | 6.2 | 0.7 | 75.7 | 8.8 | 14.9 |
| 450 | 3 | 6.2 | 12.1 | 65.9 | 8.3 | 13.8 |
| 500 | 1 | 18.1 | 7.1 | 21.3 | 5.8 | 65.7 |
| 500 | 3 | 21.5 | 47.4 | 16.8 | 3.8 | 31.9 |
| 550 | 1 | 69.8 | 17.3 | 3.0 | 1.4 | 78.3 |
| 550 | 2 | 74.9 | 22.0 | 1.6 | 1.1 | 75.3 |
| 550 | 3 | 56.0 | 31.3 | 4.5 | 1.6 | 62.6 |
| 550 | 6 | 51.9 | 24.7 | 4.1 | 1.6 | 69.6 |
| 550 | 9 | 46.5 | 18.4 | 5.3 | 2.1 | 74.3 |
| 550 | 12 | 36.2 | 17.9 | 6.3 | 2.3 | 73.6 |
| 550 | 15 | 46.8 | 7.6 | 2.5 | 1.3 | 88.6 |

Reasonable variations, such as those which would occur to a skilled artisan, can be made herein without departing from the scope of the invention.

I claim:

1. A process for converting olefins to aromatics comprising contacting an olefin reactant with a dehydrocyclizing catalyst composition comprising:
    (a) at least one bismuth component, and
    (b) at least one lanthanide component.

2. The process of claim 1 wherein the ratio of (a) to (b) is about 5:1 to about 1:5.

3. The process of claim 2 wherein the catalyst is contacted with at least one base selected from the oxides, hydroxides, and carbonates of alkali and alkaline earth metals prior to use.

4. The process of claim 3 wherein the catalyst contains at least one oxide.

5. The process of claim 4 wherein (a) is bismuth oxide and (b) is cerium oxide.

6. The process of claim 1 wherein the olefin reactant contains propylene.

7. The process of claim 5 wherein the olefin reactant contains propylene.

* * * * *